United States Patent
Adjanohoun (10) Patent No.: US 8,724,098 B2
(45) Date of Patent: May 13, 2014

(54) METHOD FOR CANDLING FERTILIZED EGGS WITH GREEN OR BLUE LIGHT AND CORRESPONDING DEVICE

(75) Inventor: Ephrem Adjanohoun, Pace (FR)

(73) Assignee: Egg-Chick Automated Technologies, Pace (FR)

( * ) Notice: Subject to any disclaimer, the term of this patent is extended or adjusted under 35 U.S.C. 154(b) by 186 days.

(21) Appl. No.: 13/058,897

(22) PCT Filed: Aug. 6, 2009

(86) PCT No.: PCT/EP2009/060242
§ 371 (c)(1),
(2), (4) Date: Feb. 14, 2011

(87) PCT Pub. No.: WO2010/018127
PCT Pub. Date: Feb. 18, 2010

(65) Prior Publication Data
US 2011/0141455 A1   Jun. 16, 2011

(30) Foreign Application Priority Data
Aug. 13, 2008 (FR) ...................... 08 55571

(51) Int. Cl.
*A01K 43/00* (2006.01)
*G01N 33/08* (2006.01)

(52) U.S. Cl.
USPC ............................. 356/55; 356/53

(58) Field of Classification Search
USPC ..................................... 356/52–68
See application file for complete search history.

(56) References Cited

U.S. PATENT DOCUMENTS

| 2,165,423 | A | * | 7/1939 | Templeman ..................... 356/66 |
| 2,370,121 | A | * | 2/1945 | Bramson ......................... 356/58 |
| 5,173,737 | A | | 12/1992 | Mitchell et al. |
| 5,745,228 | A | | 4/1998 | Hebrank et al. |
| 2005/0152918 | A1 | * | 7/2005 | Hebrank .................... 424/209.1 |
| 2006/0038978 | A1 | | 2/2006 | Zweig et al. |

FOREIGN PATENT DOCUMENTS

| FR | 786607 | 9/1935 |
| FR | 2 787 579 A1 | 6/2000 |
| FR | 2 912 217 A1 | 8/2008 |
| JP | 2001-27612 | 1/2001 |
| JP | 2004-101204 | 9/2002 |

* cited by examiner

*Primary Examiner* — Tarifur Chowdhury
*Assistant Examiner* — Michael P Lapage
(74) *Attorney, Agent, or Firm* — Patterson Thuente Pedersen, P.A.

(57) ABSTRACT

An egg candling method for determining a state of eggs between the 13$^{th}$ and the 17$^{th}$ day of incubation, particularly for identifying with certainty the living or dead state of that egg. The egg is illuminated with a green or blue light to visually show on the shell a shadow of the blood network supplying the embryo of the egg if it is present in the egg. At least one image of the egg is acquired then processed in order to determine a vitality level of the egg, based on the presence or not of this blood network and the size of the veins of said blood network. The method also determines the presence or absence of air cell in the upper portion of the egg and to thus define the inverted or uninverted position of the egg. Finally, the method also makes it possible to detect lesions on an egg shell and particularly cracked shells.

19 Claims, 4 Drawing Sheets

FIGURE 6

METHOD FOR CANDLING FERTILIZED EGGS WITH GREEN OR BLUE LIGHT AND CORRESPONDING DEVICE

PRIORITY CLAIM

The present application is a National Phase entry of PCT Application No. PCT/FR2009/060242, filed Aug. 6, 2009, which claims priority from French Application No. 0855571, filed Aug. 13, 2008, the disclosures of which are hereby incorporated by reference herein in their entirety.

TECHNICAL FIELD

The present invention relates to an egg candling method and apparatus for determining a state of eggs.

BACKGROUND ART

In the poultry industry, particularly the production of chicks, methods are known for automatic egg candling using the transparency of the egg at the end of the incubation period in order to differentiate two categories of eggs: full eggs that are opaque to light comprising not only fertilized eggs containing an entirely-developed embryo, alive or dead, but also contaminated or rotten eggs, and eggs that are permeable to light comprising unfertilized eggs, called clear eggs, but also the underdeveloped eggs containing a prematurely dead embryo. These methods consist in emitting a luminous flux towards an egg to candle and then analyze the luminous flux that has passed through the egg in order to determine its fertilized or unfertilized state, based on the luminous flux rate absorbed by the egg. With that end, the system usually comprises a device for emitting a luminous flux, a receiver for receiving the luminous flux that has passed through the egg and a processor for electronically processing the luminous flux received via the receiving means. The electronic processor is thus able to roughly differentiate the eggs according to the luminous flux rate absorbed by the egg. At the end of the incubation period, the fertilized egg containing a normally-developed living embryo is opaque. However, so are the eggs containing an embryo which died late or contaminated and rotten eggs. The latter are hence not easy to differentiate from normally-developed eggs. As for the eggs that are permeable to light at the end of the incubation period, they either correspond to infertile eggs or to eggs containing a prematurely dead embryo, without it being possible to distinguish them in a reliable manner.

This candling method by transparency thus does not make it possible to differentiate with certainty the live eggs from the dead eggs at the end of the incubation period. Moreover, it is not adapted to be used at a more premature stage of the development cycle of the egg, for example between the $3^{rd}$ and $17^{th}$ day of the incubation cycle of the hen's egg. It does not make it possible to know with certainty the fertilized or unfertilized state of the egg at the beginning of the cycle due to the insignificant size of the embryo. It does not provide either more precise data on the living or dead state of the embryo at an intermediate stage of the incubation cycle and/or on its development state (normal development or not of the embryo at this same intermediate stage of the incubation cycle). Furthermore, it is not adapted either to determine an inverted or uninverted state of the egg based on the position of its air cell. Finally, it gives no data on the integrity of the egg shell, namely the presence or not of cracks on the shell.

Alternatively, a candling carried out manually using a source of white light does not make it possible either to compensate for the aforementioned drawbacks due to the poor visibility of the inner structures of the egg.

SUMMARY OF THE INVENTION

An object of embodiments of the present invention is to propose a solution to compensate for all or part of the aforementioned drawbacks.

To this end, embodiments of the present invention include an egg candling method for determining at least a state of at least a fertilized egg containing an embryo, comprising the following steps:

a) illuminating of at least one portion of an egg with a light source having one or several wavelengths ranging between 440 and 570 nm, such as to visually show on the eggshell a shadow of a possible blood network of the embryo and acquisition of at least one image of the illuminated egg; and b) analyzing the image to determine the vitality level of the embryo of the egg, based on the presence or not of a blood network supplying the embryo of the egg in said image and, in the case of a presence of a blood network, on the size of the veins of the blood network.

One may particularly deduce if the embryo is living or dead if its vitality level is normal or not based on its age.

This wavelength interval corresponds to a blue or green light. The use of this blue or green light, advantageously under diffracted form, makes it possible to show very distinctly on the eggshell the shadow of the veins and vessels of the blood network supplying the embryo of the egg, due to the fact that they are positioned against the walls and inner membranes of the shell.

One can advantageously use a green light whereof the wavelength ranges between 510 and 570 nm, preferably between 530 nm and 550 nm. This wavelength may be used between the $3^{rd}$ and the $17^{th}$ day of the incubation cycle.

Alternatively, one may use, at a premature stage of the incubation cycle, for example between the $3^{rd}$ and $6^{th}$ day of incubation, a blue light whereof the wavelength ranges between 440 and 510 nm.

Usually, this green or blue light mainly shows 3 areas from the top to the bottom of the egg: a first very luminous area corresponding to the air cell, a second area of intermediate luminosity corresponding to the area of the egg substantially containing the embryonic fluids, the blood network supplying the living or dead embryo and, in low position of this area, an opaque mass corresponding to a portion of the body of the embryo and finally a third area which is very dark and wherein no structure is identifiable.

During the step of analysis of the image, one may detect in the image the presence or not of a network of dark intersected lines representing the shadow of the blood network and one can deduce, based on the presence or not of these dark lines and their size (thickness and/or length), the vitality level of the embryo.

According to a feature of an embodiment of the invention, the step a) comprises the illumination of the upper portion of the egg, arranged such that its revolution axis is substantially vertical, preferably by means of a light source arranged over the egg substantially on the revolution axis of the egg, and the acquisition of an image of the upper portion of the illuminated egg by a camera, arranged at the vicinity of the light source, the image acquisition axis of the camera forming an angle ranging between 0 and 70° with a reference plane that is perpendicular to the revolution axis of the egg and located at mid-distance between the flattened end and the narrow end of the egg.

Advantageously, one can provide the acquisition of at least two images of the illuminated egg, by at least two distinct cameras advantageously covering both sides of the egg to ensure that the blood network, if it is present, shows visually on at least one of the acquired images whatever its position in the egg. In this case, the step a) comprises the illumination of the egg with a green or blue light, preferably green, the acquisition by a first camera of an image I1 of the illuminated egg and the acquisition by a second camera of an image I2 of the illuminated egg, the first and second cameras being arranged facing each other on either side of a median plane of the egg comprising the revolution axis of the egg. The step b) thus comprises an analysis of both images I1 and I2 in order to determine the vitality level of the embryo of the egg.

According to a second embodiment, one can provide to excite the embryo within the egg and to acquire an image of the illuminated egg before and after excitation in order to determine whether the blood network of the egg has changed position and to deduce whether the egg is alive or dead. In fact, if the egg is alive, it reacts to the stimulus and the position of its blood network as well as the opaque mass of the body of the embryo becomes modified. In this embodiment, the step a) comprises the illumination of the egg with a green or blue light, preferably green, the acquisition of an image I1 of the illuminated egg by a camera, the excitation of the embryo of the egg by stimulus and, after excitation, the illumination of the egg with green or blue light and the acquisition of an image I'1 of the illuminated egg by the same camera. The step b) of the method of the invention comprises a comparison of both images I1 and I'1 in order to determine the living or dead state of the egg and/or to confirm the vitality level of the embryo. If the images I1 and I'1 are different, the egg is in a living state.

This embodiment with excitation of the embryo may be used with or without prior analysis of the size of the veins of the network to determine the living or dead state of the egg.

Advantageously, in this embodiment, at least two images by two distinct cameras before excitation of the embryo and at least two images by these same cameras after excitation are acquired in order to ensure that the blood network, if it is present within the egg, is visible on at least one of the images prior to excitation and after excitation. In this case, step a) comprises the illumination of the egg with a green or blue light, preferably green, the acquisition of an image I1 of the illuminated egg by a first camera and the acquisition of an image I2 of the illuminated egg by a second camera, the excitation of the embryo of the egg by stimulus, and, after excitation, the illumination of the egg with said green or blue light, the acquisition of an image I'1 of the illuminated egg by the first camera and the acquisition of an image I'2 of the illuminated egg by the second camera. The step b) of the method of the invention comprises a comparison of both images I1 and I'1 and/or a comparison of both images I2 and I'2 to determine the living or dead state of the egg and/or to confirm the vitality level of the embryo.

For the excitation step, the stimulus used is a temporary disturbance to the neighboring surroundings of the embryo triggering or amplifying its movement inside the egg. It may for example take the form of a luminous, sound and/or thermal wave or of a vibration triggered for example by a shock or any other type of stimulus leading to a movement of the embryo. The stimulus is for example an intense luminous and/or thermal signal, such as a white light or a laser signal.

According to an improvement applicable to all the embodiments, the step b) further comprises an analysis of the image or images in order to determine the presence or not of an air cell in the upper portion of the egg and deduce whether the egg is in an inverted or uninverted state and possibly whether the air cell is shifted with respect to the vertical axis of the egg.

According to an improvement applicable to all the embodiments, the step b) further comprises an analysis of the image or images in order to analyze the integrity of the shell and locate cracks which let light out more intensely.

According to a specific embodiment, for two neighboring eggs, the illumination is carried out alternately between both eggs.

Embodiments of the invention also relate to an automatic egg candling device for determining a state of a fertilized egg, comprising:
  an illumination device comprising at least a light source having one or several wavelengths ranging between 440 nm and 570 nm, preferably ranging between 510 and 570 nm, to illuminate an egg such as to visually show a shadow of the blood network of the embryo of the egg on the shell of the egg;
  an image acquisition receiver to acquire at least one image of the illuminated egg; and
  an image analyzer to determine, based on the shadow, a vitality level of the embryo of the egg.

According to a specific embodiment, the device further comprises:
  a conveyor for transporting, according to a conveying plan and a direction of movement, trays comprising cells wherein are arranged eggs to be candled,
  a support arranged above the conveyor, fixedly bearing the illumination device comprising at least a ramp of light sources and the image acquisition receiver comprising at least a ramp of cameras, the ramp of light sources and the ramp of cameras being arranged parallel or transverse to the direction of movement, and
  a displacement device able to vertically move the support between a raised position and a candling position wherein the light sources abut against the upper portion of the eggs positioned facing each other in the cells.

In embodiments, the displacement device is able to move the support parallel and/or transverse to the direction of movement, and/or the image acquisition receiver comprises two ramps of cameras arranged symmetrically on either side of the ramp of light sources, the image acquisition axis of the cameras forming an angle ranging between 0 and 70° with conveyor plane of the trays. This device enables maintenance of the same distance between the camera and the egg, regardless of the position of the egg in the trays and regardless of the type of trays.

In embodiments, the illuminating device includes the ability to adjust the luminosity (light intensity) of the light source.

In embodiments, the illuminating device includes the ability to hermetically guide the light produced by the light source towards the egg so as to minimize pollution of the neighboring surroundings of the egg.

The invention will be better understood and other objects, details, characteristics and advantages will become more apparent in the following detailed explanatory description of both specific embodiments of the invention, with reference to the accompanying schematic drawings.

DETAILED DESCRIPTION

An egg is illuminated with a green light in order to visually show on the shell a shadow of the blood network supplying the embryo of the egg if it is present in the egg. At least one image of the egg is acquired and then processed in order to determine, based on the presence or not of this blood network and its size, whether the egg is in a living or dead state.

Figure 1:
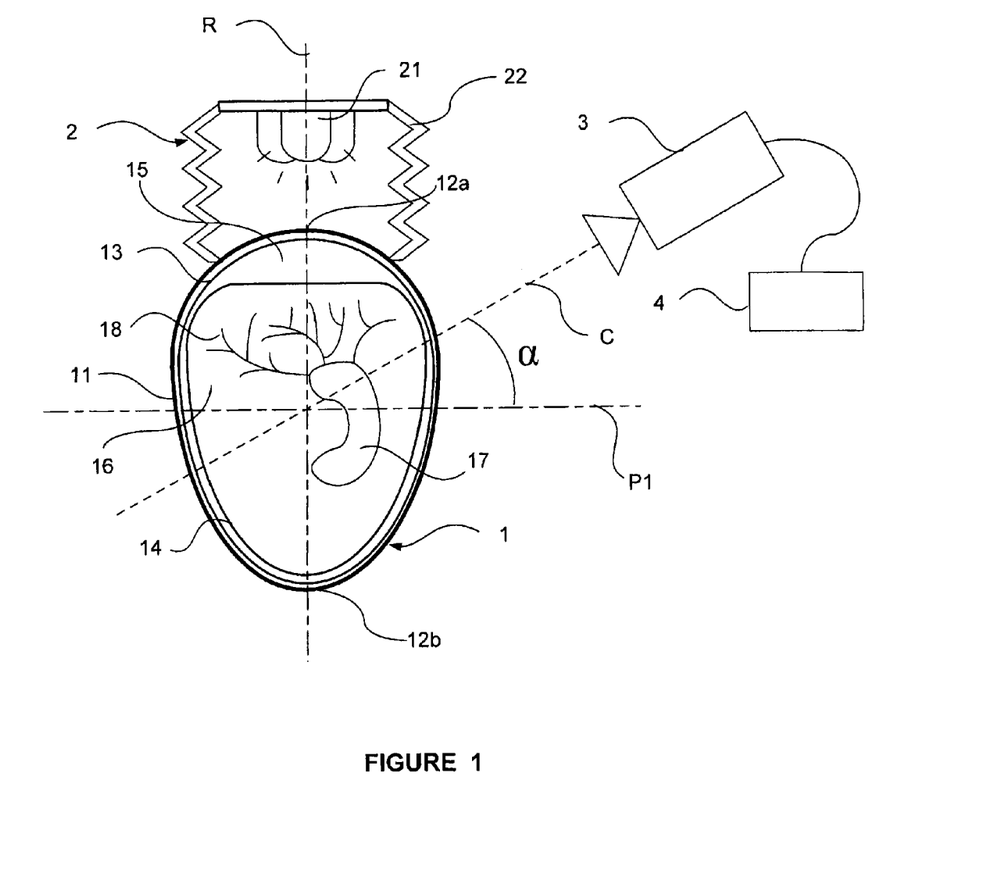
FIG. 1 is a block diagram depicting an embodiment of the method of the invention.

Referring to FIG. 1, the candled egg is a fertilized egg 1 represented schematically. It comprises a shell 11 of ovoid shape exhibiting a flattened end 12a and a narrow end 12b. A very fine outer membrane of the shell 13 covers the inside of the shell 11. An equally fine inner membrane of the shell 14 partially covers the outer membrane of the shell 13 and is separated from it at the apical pole of the egg such as to form an air cell 15 at the flattened end 12a of the egg. The air cell 15 appears very luminous when it is illuminated by a green or blue light. The inner membrane of the shell 14 delimits a pocket 16 enclosing, apart from the white and the transparent embryonic liquids in the upper portion and the yolk in the lower portion, an embryo 17 in intermediary position above the yolk, which embryo is supplied by a blood network 18 comprising veins and capillary vessels. The blood network is mainly arranged against the inner membrane of the shell 14. It is thus very close to the shell and bathes in the transparent amniotic liquids.

The egg 1 is arranged such that its revolution axis, marked R, is substantially vertical. A reference plane P1, perpendicular to the revolution axis R and crossing this axis at a point located at mid-distance between the flattened end 12a and the narrow end 12b of the egg, is presented. The portion of the egg 1 located above the reference plane P1, called the upper portion of the egg, is illuminated by a light source 2 arranged above the egg substantially on the revolution axis R. The light source 2 is a source of green or blue light whereof the wavelength(s) is/are comprised between 440 nm and 570 nm, preferably 510 nm and 570 nm. This light is particularly advantageous for showing the veins and vessels of the blood network 18 located at the periphery of the inner side of the shell. This light, which is advantageously diffracted, is absorbed by the elements of the egg transporting the blood. When the egg is illuminated with this green or blue light, a shadow of the blood network appears on the egg shell. The presence or not of this blood network and the size (thickness and/or length) of the veins of the network make it possible to determine the living or dead state of the embryo. The air cell also appears very luminous.

The light source 2 is for example formed by one or several light-emitting diodes 21. The wavelength range of the light emitted by the source 11 ranges between 440 nm and 570 nm. The light emitted is either monochromatic (1 single wavelength in this range) or polychromatic (several wavelengths in this range). The light used is advantageously a green light whereof the length ranges between 510 and 570 nm, preferably between 530 nm and 550 nm. At a premature stage of the incubation cycle, for example between the $3^{rd}$ and the $6^{th}$ day of incubation, it is nevertheless possible to use a blue light whereof the wavelength ranges between 440 and 510 nm.

The light source 2 is advantageously equipped with a tubular-shaped cup 22 with a bellow abutting against the flattened end 12a of the egg during its illumination. This cup forms a light guide between the light source 2 and the egg 1 and makes it possible to prevent light losses as well as influxes of parasitic light. This cup is for example achieved in black elastomer.

According to the invention, an image of the upper portion of the egg where the shadow of the blood network 18 appears on the shell is acquired by a black and white camera or a color camera 3 arranged at the vicinity of the upper portion of the egg 1. The image acquisition axis, marked C, of camera 3 preferably crosses the revolution axis R at its intersection with the reference plane P1. The image acquisition axis C forms an angle α, called angle of latitude, with the reference plane P1. This angle ranges between 0° and 70°. If the egg 1 is arranged in a tray comprising other eggs, the walls of the tray as well as the other eggs may prevent the acquisition of the upper portion of the egg 1. In this case, one chooses an angle α in the upper portion of the range [0°,70°], for example an angle ranging between 30° and 70°. Another solution is to provide for raising the egg in order to position the upper portion of the egg in the field of the camera lens.

An image processor 4 is connected to the camera 3 in order to process the acquired image and determine, based on the latter, whether the embryo 17 is living or dead.

According to a first embodiment which will be described in detail further on in the description, the processing carried out by the image processor 4 comprises determining whether a network of dark lines corresponding to the blood network of the egg is present in the acquired image, and estimating the thickness and/or length of the veins and comparing this or these value(s) to one or several reference values depending on the age of the egg. If the estimated thickness value and/or the estimated length value is or are higher than the reference thickness value and/or the reference length value, the egg is in a living state. Otherwise, it is determined to be in a dead state.

According to a second embodiment also described in detail further on in the description, the embryo of the egg is excited and an image acquisition is carried out before and after excitation of the embryo. The image processing step of the method hence includes comparing the image before excitation and the image after excitation. If the egg is living, the embryo will react to the excitation and its blood network as well as the dark mass of the embryo moves between both images. Both images are thus different. If both images are identical, the egg is determined to be dead.

These two embodiments may be applied together or separately. These two embodiments are described in detail afterwards.

First Embodiment

Figure 2:
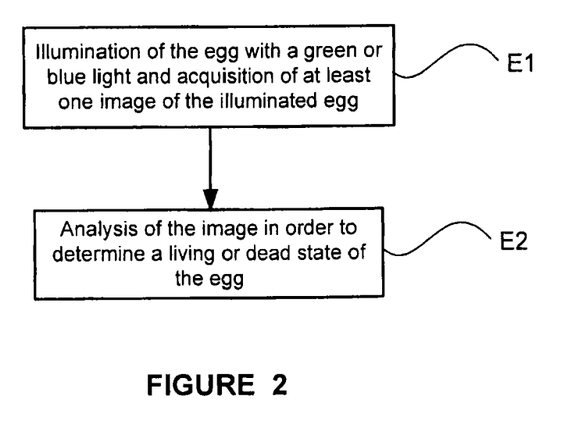
FIG. 2 is a flowchart depicting the steps of the method of the invention according to a first embodiment.

According to this first embodiment illustrated by FIG. 2, the method of the invention comprises a step E1 of illuminating at least one portion of the egg to be candled with a green or blue light, preferably green with a length ranging between 530 nm and 550 nm, such as to visually show on the shell of the egg a shadow of the blood network of the embryo if it is present in the egg and acquire at least one image of the illuminated egg; and a step E2 of analyzing the acquired image in order to determine the presence or not of a blood network in the egg and deduce a living state or a dead state of the egg. The step E2 comprises quantifying the image as to the thickness and/or the length of the dark lines representing the shadow of the blood network of the egg on the shell and comparing these values to reference values which depend on the age of the egg. For a given age, if the thickness value is lower than the reference thickness value for this age and/or if the length value is lower than the reference length value for this age, the egg is considered to be dead. Otherwise, it is considered to be living. These reference values increase specifically with the age of the egg.

According to an improvement, several reference thickness values and/or several reference length values are defined for each stage of the incubation cycle of the egg in order to characterize, more subtly, the vitality level of the embryo at a given stage of the incubation cycle, with the rule being that, at a given age and below a given threshold, the thinner and/or the shorter the veins of the blood network, the weaker the vitality level of the embryo. Beyond this threshold, the embryo is considered to be alive and strong. Thus, the size of the veins estimated at step E2 is compared to these different reference values and the result of this comparison enables determination of a vitality level of the embryo.

According to an improvement, at least two images of the illuminated egg are acquired by cameras having different acquisition angles. It may occur that, according to the position of the embryo in the egg and according to the acquisition angle of the camera 3, the blood network is not visible or is hardly visible in the image acquired by the camera 3. One can thus advantageously take another image of the illuminated egg by another camera arranged, for example, opposite camera 3 with respect to the vertical median plane of the egg.

According to an improvement, the step E1 comprises the illumination of the egg with a green or blue light and the acquisition of an image I1 of the illuminated egg by a first camera, for example camera 3, and the acquisition of an image I2 of the illuminated egg by a second camera, not shown on FIG. 1, the said first and second cameras being symmetrically arranged on either side of the revolution axis of the egg. The step E2 comprises an analysis of two images I1 and I2 to determine the presence or not of a blood network and to deduce a living state or a dead state of the egg.

Second Embodiment

Figure 3:
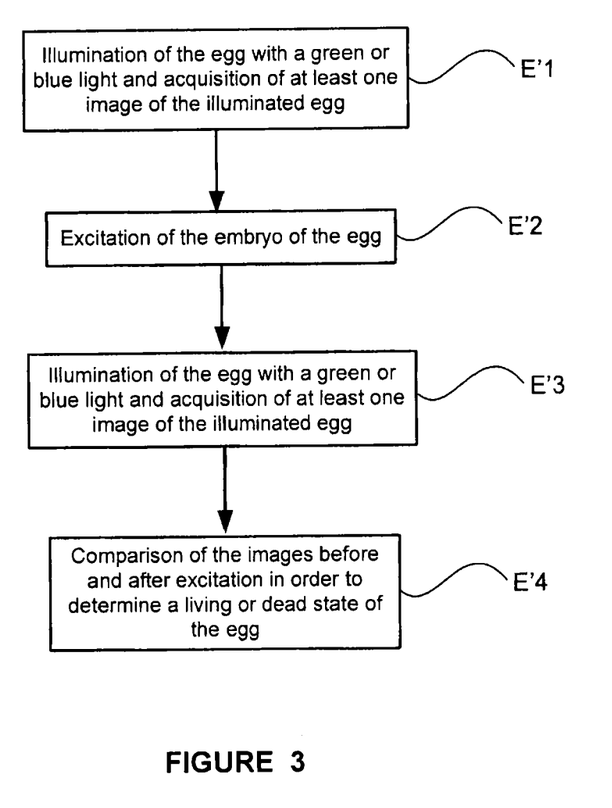
FIG. 3 is a flowchart depicting the steps of the method of the invention according to a second embodiment.

According to this second embodiment, illustrated by FIG. 3, the method of the invention comprises a step E'1 of illuminating the egg with a green or blue light and of acquisition of at least one image I1 of the illuminated egg by a camera, a step E'2 of excitation of the embryo of the egg by a stimulus, a step E'3 of illuminating the egg with the green or blue light and of acquiring, after excitation of the embryo, an image I'1 of the illuminated egg by the same camera, and a step E'4 of comparison of both images I1 and I'1 to deduce the living or dead state of the egg. If the embryo is living, the blood network and the opaque mass of the embryo change positions in the egg between images I1 and I'1. If images I1 and I'1 are different, one may thus deduce that the egg is in a living state.

The stimulus employed in step E'2 is a temporary disturbance of the neighboring surroundings of the embryo. It may take the form of a luminous, sound and/or thermal wave or of a vibration triggered for example by a shock or any other type of stimulus leading to a movement of the embryo. The stimulus is for example an intense luminous and/or thermal signal, such as a white light or a laser signal. This stimulus is preferably a laser signal. The mechanism for generating this stimulus are advantageously provided in the light source 2. Such mechanism can include, for example, a source of white light or a laser diode arranged beside green or blue light-emitting diodes of the light source 2.

According to an improvement, at least two images of the egg are acquired at different image acquisition angles before and after excitation. According to this improvement, the step E'1 comprises the illumination of the egg with a green or blue light, the acquisition of an image I1 of the illuminated egg by a first camera and the acquisition of an image I2 of the illuminated egg by a second camera. The step E'2 of excitation remains unchanged. Step E'3 comprises the illumination of the egg with the green or blue light, the acquisition of an image I'1 of the illuminated egg by the first camera and the acquisition of an image I'2 of the illuminated egg by the second camera. Step E'4 thus comprises a comparison between both images I1 and I'1 and/or a comparison of both images I2 and I'2 in order to determine the living state or the dead state of the egg. If the blood network and the opaque mass of the embryo have changed position between images I1 and I'1 or between images I2 and I'2, the egg is in a living state.

Alternatively, step E'4 comprises an analysis of two images I1 and I2 and/or two images I'1 and I'2 in order to determine, based on the dark lines they contain, whether the egg is in a living or dead state, then a comparison of both images I1 and I'1 and/or both images I2 and I'2 to validate the living or dead state determined by the analysis.

This second embodiment may come as a complement to the first embodiment to confirm the vitality level determined during the analysis of the size of the blood network veins. According to an improvement applicable to both embodiments, step E2 and E'4 further comprise an analysis of at least one of the images I1, I2, I'1 and I'2 in order to determine the position of the air cell 15 of the egg and to deduce whether the egg is in an inverted state or an uninverted state. The egg is defined as being in an inverted state when its air cell 15 is localized in the lower portion of the egg and as being in an uninverted state when its air cell is localized in the upper portion of the egg. The detection of this state is important for injecting vaccines into the egg and/or its topping. Hence, the image analysis consists in detecting whether the upper portion of the egg comprises or not a very luminous area corresponding to the air cell of the egg. If such an area is detected in the upper portion of the egg, the latter is in an uninverted position. The image analysis may also enable to see whether the air cell is shifted with respect to the vertical axis of the egg.

According to another improvement applicable to both embodiments, step E2 or E'4 further comprises an analysis of at least one of the images I1, I2, I'1 and I'2 in order to check the integrity of the egg shell and detect the possible presence of cracks. These cracks have as a characteristic the passing of light pass therethrough. The detection of cracks thus consists in detecting the presence of highly intense luminous lights in the acquired images.

Figure 4:
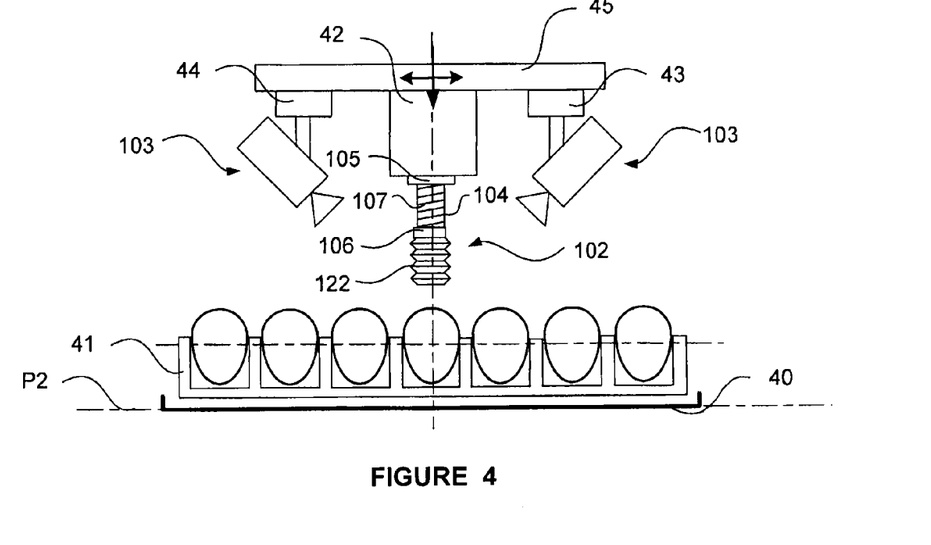
FIG. 4 is a side view, perpendicular to the direction of movement of the trays, of a device able to implement embodiments of the method of the invention, wherein the support of the ramp of the light sources and the ramp of the cameras is in a raised position.
Figure 5:
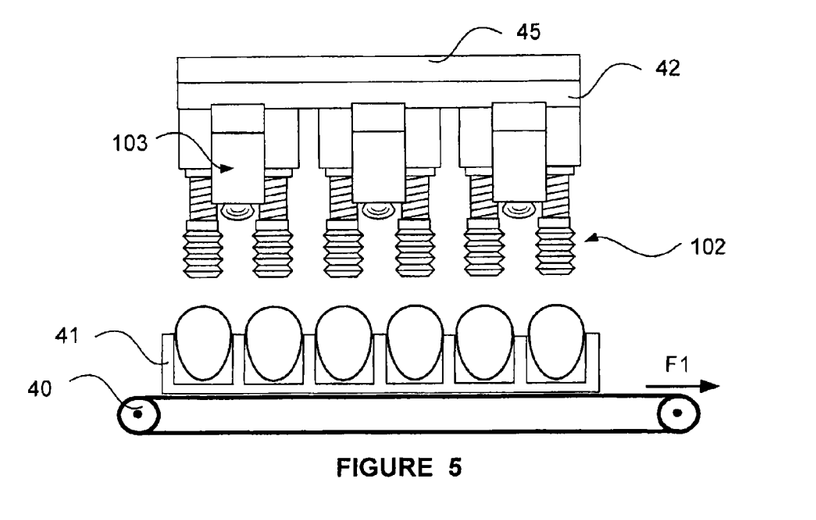
FIG. 5 is a side view, parallel to the direction of movement of the trays, of the device represented on FIG. 4.
Figure 6:
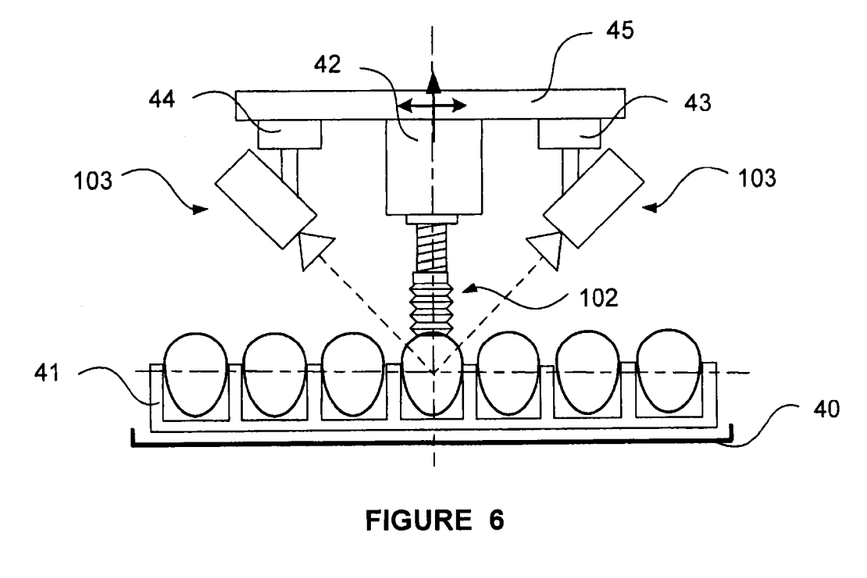
FIG. 6 is a view analogous to that of FIG. 4, wherein the support of the ramp of the light sources and the ramp of the cameras is in a candling position.

FIGS. 4 to 6 schematically represent an automatic candling device able to implement the method of the invention. FIGS. 4 and 5 respectively represent side views, respectively transversal and parallel to the direction of movement of the trays, of the device in raised position and FIG. 6 represents a side view that is analogous to that of FIG. 4 wherein the device is in candling position. The device comprises a conveyor 40 for transporting egg incubation trays 41, according to a conveying path along which are arranged an illuminating device 102 and image acquisition receiver 103 of the illuminated eggs. An image processor, not represented on FIGS. 4 and 6, is provided for processing the acquired images.

The conveyor 40, comprising for example an endless belt type conveyor, defining a conveying plane P2 (FIG. 4) of trays, is able to move the trays 41 in the direction of movement F1. The trays comprise, for example, longitudinal rows of cells, the rows being aligned or shifted apart (cells arranged in staggered rows). In the illustrated example, the tray comprises 7 aligned rows of 6 eggs arranged parallel to the direction of movement F1.

The illuminating device 102 and the image processor 103 are adapted to process the eggs one row at a time. The illuminating device 102 is constituted of a row of light sources arranged side by side on a horizontal illumination ramp 42. In the illustrated example, the illumination ramp is placed parallel to the direction of movement F1 above the conveying path. A light source 102 is provided for each egg of a same row. Each light source 102 comprises a tube 104 comprising at its upper end a base 105 for fixing the tube 104 to the ramp 42 and bearing at its lower end one or several light-emitting diodes mounted on a bushing 106. The bushing 106 is slidingly mounted on the tube 104 and is elastically stressed by a spring 107 mounted between the base 105 and the bushing 106. The bushing 106 is preferably equipped with a cup 122 in the shape of a bellow for guiding the light produced by the diode(s) towards the egg and to come into contact with the upper portion of the egg when the illumination ramp 42 is lowered (candling position).

The image processor 103 is constituted of a plurality of cameras arranged on at least one horizontal ramp 43. The ramp 43 is placed parallel to the direction of movement F1 above the conveying path. A camera of the ramp is provided for each egg or for each group of eggs of the row arranged side by side. In the illustrated example, a camera is provided for two eggs. Advantageously, a second horizontal ramp 44 fitted with cameras is symmetrically arranged on the ramp 43 of cameras with respect to the ramp of light sources. The cameras are intended to acquire an image of the upper portion of the eggs of the row.

The ramps of the cameras 43 and 44 and the ramp of the light sources 42 are mounted on a support 45 able to move vertically between a raised position (high position) and a candling position (low position) and transversally. The movement of the support 45 is controlled by a controller, not shown on FIGS. 4 to 6. The controller also controls the lighting of the light sources and the image acquisition by the cameras. It is worth noting that the controller may be gathered with the image processor 4 in a central controlling unit of the device.

In operation, a tray is channeled, under the support 42, the support being in a raised position with the light sources of the illumination ramp 42 positioned over a row of eggs of the tray. The controller moves the support vertically downwards until the cup of the light sources abuts against the upper portion of the eggs of the row. The support is thus in candling position (low position). The light sources are thus on. The cameras arranged symmetrically on either side of the light sources thus acquire, successively or simultaneously, images of the illuminated eggs. Then the controller moves the support 45 vertically upwards to its raised position (high position) then transversally to position the light sources above the following row of eggs. The images acquired by the cameras are transmitted by the image processor as they are acquired or after they acquire images of the set of eggs of the tray. When all the rows of the tray have been processed, the conveyor is activated in order to channel a new tray to be processed.

In the illustrated example, one single camera is provided for each pair of neighboring eggs of a row. One thus preferably provides an alternated illumination between both eggs of the pair and a separate image acquisition for both eggs. First, an egg is illuminated, then an image is acquired for this egg with the camera, then the other egg is illuminated and an image acquisition is carried out for it. Thus, for a row of eggs, all the even eggs of the row are first simultaneously illuminated then all the uneven eggs are simultaneously illuminated.

For processing shifted trays wherein the eggs of two successive rows are arranged in staggered rows, the displacement device is further able to longitudinally move the support 45 to pass from one row to the next. It is also possible to provide two ramps of light source, mounted on the same support or each on a support, the light sources of both ramps being longitudinally shifted with respect to each other and each ramp of light sources being associated to one or two ramps of cameras.

Advantageously, the light sources are provided with the ability to make the luminosity vary in order to refine the quality of the images taken by the cameras.

Advantageously, several images may be taken in the same position by the same camera, the only difference between them being the luminous intensity of the light sources, namely the duration of exposure used for the image acquisition, in order to refine the quality of the details for the analysis of the blood network and/or of other accessory elements within the egg.

For the implementation of the second embodiment of the method of the invention (with excitation of the embryo), the light sources and the illuminating ramp are equipped with excitation means such as a laser diode.

According to an improvement, the device is equipped for raising the eggs in order to facilitate the image acquisition when the eggs are close together, for example when they are arranged in staggered rows in the incubation trays, or when the size of the eggs surrounding the egg to be analyzed hinders the image acquisition, for example when a very large egg is arranged in front of a small-sized egg to be analyzed.

Although the invention has been described in connection with different particular embodiments, it is to be understood that it is in no way limited thereto and that it includes all the technical equivalents of what has been described as well as combinations that fall within the scope of the invention. The ramps of the light sources and cameras can be arranged transverse in the direction of movement F1 of the conveyor and to move, in order to pass from one row of eggs to the next, the conveyor instead of moving the ramps. Several rows of eggs can be processed at the same time by using more ramps of light sources and ramps of cameras.

The invention claimed is:

1. A method for candling eggs to determine at least a state of at least a fertilized egg containing an embryo, comprising:
   illumination of said egg with light limited to one or several wavelengths not less than 440 nm and not greater than 570 nm and acquisition of at least one image of said illuminated egg;
   analysis of said image in order to determine a vitality level of the embryo of said egg based on the presence or not of a blood network supplying the embryo of said egg in said image and, in the case of the presence of a blood network, on the size of the veins of said blood network;
   analysis of said image to quantify a thickness, a length or both the thickness and the length of dark lines representing a shadow of the blood network on a shell of said egg; and
   comparison of the thickness, the length or both the thickness and the length to reference values that depend on an age of said egg.

2. The method according to claim 1, wherein the light is a green light limited to one or several wavelengths ranging not less than 510 nm and not greater than 570 nm.

3. The method according to claim 2, wherein the light is a green light limited to one or several wavelengths not less than 530 nm and not greater than 550 nm.

4. The method according to claim 1, wherein the light is a blue light limited to one or several wavelengths not less than 440 nm and not greater than 510 nm.

5. The method according to claim 1, wherein the step a) comprises the illumination of the upper portion of the egg arranged such that its revolution axis is substantially vertical, by a light source arranged above the egg substantially on the revolution axis of said egg, and the acquisition of an image of the upper portion of the illuminated egg by a camera, arranged in the vicinity of the light source, the image acquisition axis of the camera forming an angle ($\alpha$) ranging between 0 and 70° with a reference plane perpendicular to the revolution axis of the egg and located at mid-distance from the flattened end and the narrow end of the egg.

6. The method according to claim 1, wherein the step a) comprises the illumination of said egg with a green or blue light, the acquisition of a first image of said illuminated egg by a first camera and the acquisition of a second image of said illuminated egg by a second camera, said first and second cameras being arranged facing each other on either side of a median plane of the egg comprising the revolution axis of said egg,
and wherein the step b) comprises an analysis of both the first and second images to determine the vitality level of the egg.

7. The method according to claim 1, wherein step a) comprises:
the illumination of said egg with a green or blue light and the acquisition of a first image of said illuminated egg by a camera,
the excitation of the embryo of the egg by a stimulus, and, after said excitation,
the illumination of said egg with said green or blue light and the acquisition of the embryo, of second image of said illuminated egg by said camera,
and wherein step b) comprises a comparison of the first and second images to confirm the vitality level of the embryo.

8. The method according to claim 7, wherein step a) includes:
the acquisition of a third image of said illuminated egg by a second camera,
after said excitation, the acquisition of a fourth image of said illuminated egg by the second camera,
and wherein step b) comprises a comparison of the first and second images and a comparison of the third and fourth images to confirm the vitality level of the embryo.

9. The method according to claim 7, wherein the stimulus is a sound and/or light and/or thermal signal.

10. The method according to claim 7, wherein step a) includes:
the acquisition of a third image of said illuminated egg by a second camera,
after said excitation, the acquisition of a fourth image of said illuminated egg by the second camera,
and wherein step b) comprises a comparison of the first and second images or a comparison of the third and fourth images to confirm the vitality level of the embryo.

11. The method according to claim 1, wherein step b) further comprises an analysis of said image(s) in order to determine the position of the air cell of the egg and to deduce an inverted state or an uninverted state of the egg.

12. The method according to claim 1, wherein for two neighboring eggs, the illumination is carried out in an alternated manner between the eggs.

13. An automatic egg candling device for determining at least a state of a fertilized egg, comprising:
a limited spectrum source of illumination emitting light limited to a green or blue light for illuminating the egg;
a camera for acquiring at least one image of said illuminated egg; and
an image processor that is programmed to determine, based on the presence or not of a blood network supplying the embryo of the egg in said image and, in the case of presence of a blood network, of the size of the veins of said blood network, a vitality level of the embryo of said egg; and
further programmed to perform analysis of said image to quantify a thickness, a length or both the thickness and the length of dark lines representing a shadow of the blood network on a shell of said egg and to compare the thickness, the length or both the thickness and the length to reference values that depend on an age of said egg.

14. The device according to claim 13, comprising:
a conveyor that transports, according to a conveyor plan and a direction of movement, trays comprising cells wherein are arranged eggs to be candled,
a support arranged above the conveyor, bearing the limited spectrum source of illumination comprising at least a ramp of light sources and the camera comprising at least a ramp of cameras, said ramp of light sources and said ramp of cameras being arranged parallel or transverse to the direction of movement, and
the support being vertically shiftable between a raised position and a candling position wherein the light sources abut against the upper portion of the eggs positioned facing each other in the cells.

15. The device according to claim 14, wherein said support is shiftable parallel and transverse to the direction of movement.

16. The device according to claim 14, wherein said camera comprises two ramps of cameras arranged symmetrically on either side of the ramp of light sources, the acquisition axis of the cameras forming an angle ($\alpha$) ranging between 0 and 70° with a horizontal plane of the conveying means.

17. The device according to claim 14, wherein said support is shiftable parallel or transverse to the direction of movement.

18. The device according to claim 13, wherein the limited spectrum source of illumination has variable luminosity.

19. The device according to claim 13, wherein the limited spectrum source of illumination comprises a guide that directs the light produced by the light source towards the egg.

* * * * *